United States Patent
Gesswein

(10) Patent No.: US 7,824,391 B2
(45) Date of Patent: Nov. 2, 2010

(54) ARTICULATING GUIDE CATHETER

(75) Inventor: Douglas Gesswein, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1458 days.

(21) Appl. No.: 10/394,630

(22) Filed: Mar. 21, 2003

(65) Prior Publication Data

US 2004/0186378 A1    Sep. 23, 2004

(51) Int. Cl.
*A61M 25/00* (2006.01)
(52) U.S. Cl. .................................. 604/523; 604/95
(58) Field of Classification Search ......... 604/523–532, 604/536, 96.01–103.14, 95.03
See application file for complete search history.

(56) References Cited

U.S. PATENT DOCUMENTS

| | | | |
|---|---|---|---|
| 3,665,928 A * | 5/1972 | Del Guercio | 604/95.03 |
| 4,906,230 A * | 3/1990 | Maloney et al. | 604/95.03 |
| 4,983,165 A * | 1/1991 | Loiterman | 604/95.03 |
| 5,179,961 A | 1/1993 | Littleford et al. | |
| 5,308,323 A * | 5/1994 | Sogawa et al. | 604/95.03 |
| 5,389,090 A | 2/1995 | Fischell et al. | |
| 5,571,161 A | 11/1996 | Starksen | |
| 5,775,327 A | 7/1998 | Randolph et al. | |
| 6,021,340 A | 2/2000 | Randolph et al. | |
| 6,066,126 A | 5/2000 | Li et al. | |
| 6,122,552 A | 9/2000 | Tockman et al. | |
| 6,126,635 A | 10/2000 | Simpson et al. | |
| 6,287,319 B1 | 9/2001 | Aboul-Hosn et al. | |
| 6,290,697 B1 | 9/2001 | Tu et al. | |
| 6,416,511 B1 | 7/2002 | Lesh et al. | |
| 6,530,914 B1 | 3/2003 | Mickley | |

* cited by examiner

*Primary Examiner*—Kevin C Sirmons
*Assistant Examiner*—Phillip Gray
(74) *Attorney, Agent, or Firm*—Hollingsworth & Funk, LLC

(57) ABSTRACT

A guiding catheter system uses one or more steering lumens embedded within the walls of a flexible shaft. The steering lumens are in fluid contact with inflation lumens that are accessible from a proximal part of the guide catheter. The catheter is steered by pressurizing or depressurizing the inflation lumens, thereby inflating or deflating the steering lumens. The change in steering lumen pressure causes a change of the catheter's distal end, allowing the catheter to be steered.

20 Claims, 4 Drawing Sheets

Section 2-2

ARTICULATING GUIDE CATHETER

FIELD OF THE INVENTION

The invention relates generally to guiding catheter systems, and more particularly to guiding catheters for accessing the coronary sinus from the right atrium.

BACKGROUND OF THE INVENTION

Guiding catheters are instruments that allow a physician to locate and cannulate vessels in a patient's heart for performing various medical procedures, including venography and implanting of cardiac pacing devices. Cannulating heart vessels requires navigating a small diameter, flexible guide through convoluted vasculature into a heart chamber, and then into a destination heart vessel. Once the destination heart vessel is reached, the catheter acts as a conduit for insertion of payloads into the vessel.

A pre-shaped guiding catheter is typically used to locate the destination vessel. A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations.

When using pre-shaped catheters in procedures, the clinician may need to try more than one shape if difficulties are encountered. Finding and cannulating the coronary sinus, for example, can become a time consuming, trial and error procedure even in a healthy patient. Patients exhibiting symptoms of advanced heart disease can have blockages or deformations of heart structure, further complicating the task of locating the ostium. A major goal of guiding catheter design is to enable clinicians to find and cannulate a vessel of interest in the least amount of time.

Guiding catheters sometimes utilize steering tendons or wires to assist in directing the distal end of the catheter during cannulation. Although this method can be effective, the wires and associated hardware take up valuable space in the guide lumen of the catheter. Also, the relatively long and potentially convoluted passageways traversed by guide catheters lead to complication in the use of steering wires, including pull friction and mechanical backlash.

There is a need for a guide catheter with a maneuverable distal end that does not utilize pull wires. The present invention fulfills these and other needs, and addresses other deficiencies of prior art implementations and techniques.

SUMMARY OF THE INVENTION

To overcome the limitations in the prior art described above, and to overcome other limitations that will become apparent upon reading and understanding the present specification, the present invention discloses a steerable guiding catheter that can provide access to venous structures for medical procedures.

In one embodiment, a guiding catheter includes a flexible shaft having a wall, an open lumen, and a pre-shaped distal portion. One or more steering lumens are disposed within the wall of the flexible shaft proximate the pre-shaped distal portion. One or more inflation lumens are in fluid connection with the steering lumens. The inflation lumens are accessible at a proximal end of the shaft. Changing a fluid pressure of the steering lumens alters a shape of the pre-shaped distal end.

The wall of the flexible shaft may include an inner liner and an outer sheath. The steering lumens can be disposed between the inner liner and the outer sheath. An intermediate sheath may also be included between the inner liner and the outer sheath. The steering lumens are formed by one or more voids in the intermediate sheath. In one arrangement, the intermediate sheath includes longitudinally disposed ribs forming the steering lumens.

The steering lumens may be configured to be independently inflatable. In one arrangement, the one or more steering lumens include four steering lumens equally distributed around a perimeter of the flexible shaft.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
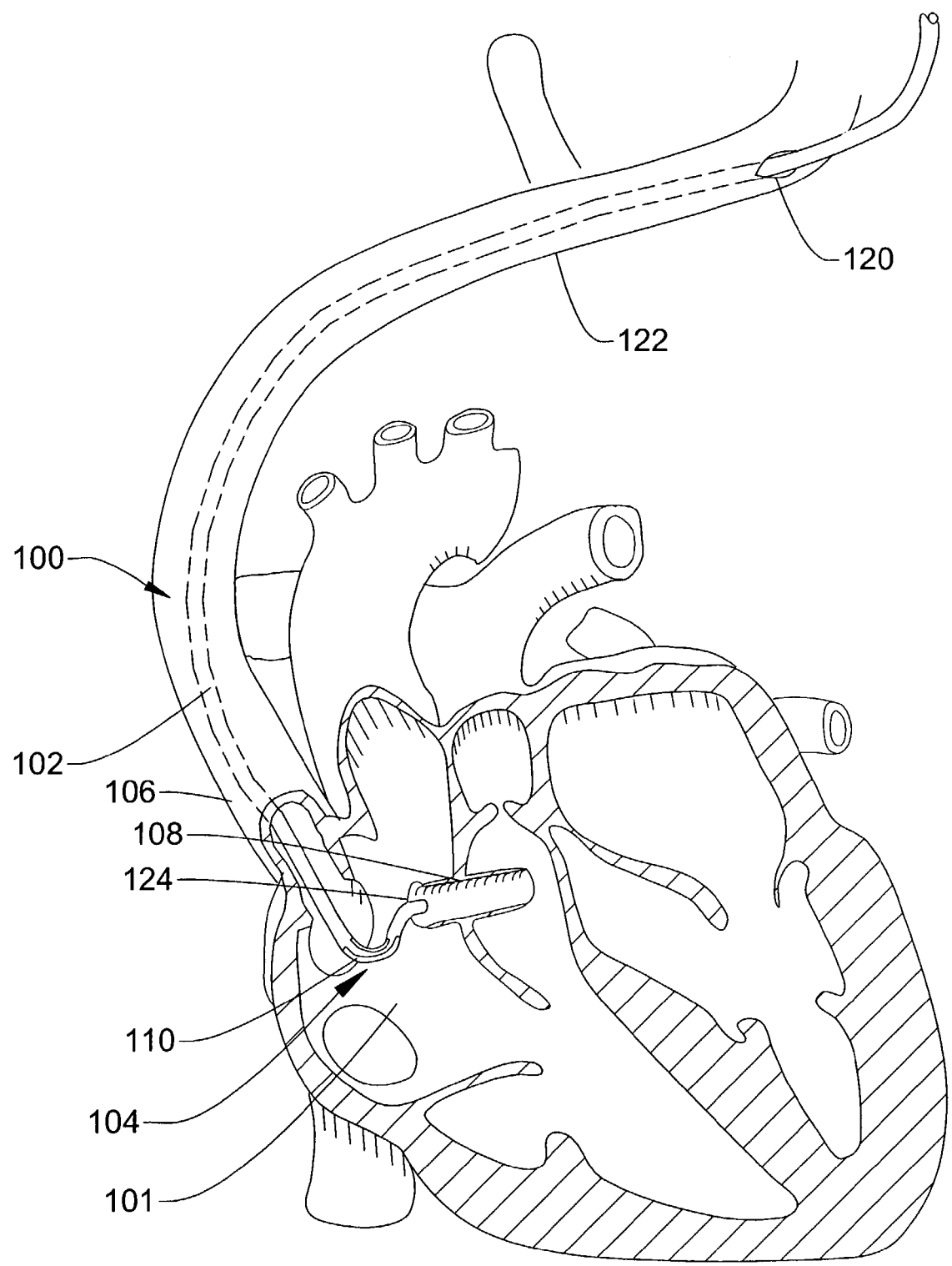
FIG. 1 is a cutaway view of a heart, showing a guiding catheter according to an embodiment of the present invention deployed in the superior vena cava and right atrium.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, a guiding catheter system of the present invention employs an inflatable lumen on a distal portion of the catheter shaft. The inflatable lumen can be pressurized to assist in steering the catheter's distal end. The catheter's shape and steering features are useful when used in accessing heart vessels such as the coronary sinus.

Referring now to FIG. 1, a guide catheter, generally indicated by reference numeral 100, is shown deployed in the right atrium 101 of the heart. The guide catheter 100 includes a flexible shaft 102 and has a distal end 104. The distal end 104 may include pre-formed bends that can be optimized for the intended path and anatomical variations along this path. In the example of FIG. 1, the catheter 101 is shown entering the right atrium 101 via the superior vena cava 106 and positioned to cannulate the coronary sinus 108.

The catheter 100 includes one or more steering lumens 110 disposed at a distal portion of the flexible shaft 102. The steering lumens 110 are inflatable by pressurizing one or more inflation lumens (not shown) of the shaft 102. Pressurization of the steering lumens 110 causes deflection of the catheter's distal end 104. The catheter 100 may include a single mode of deflection, where all of the steering lumens 110 are inflated at the same time. The catheter 100 may also be arranged with one or more independently inflatable steering lumens 110, so that multiple deflection modes can be achieved by independent pressurization/depressurization of the respective steering lumens 110.

Figure 2:
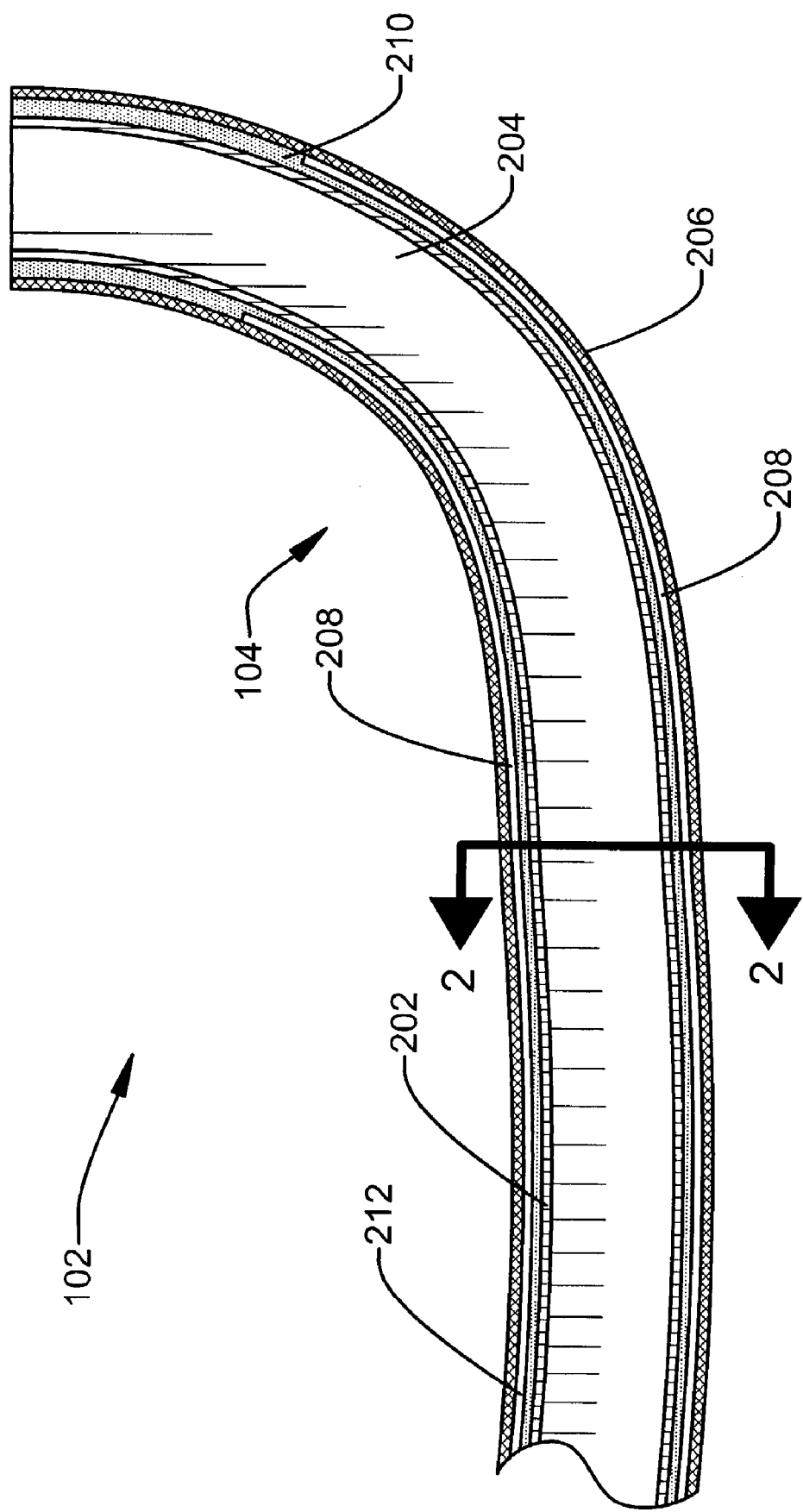
FIG. 2 is sideways cross sectional view of a guide catheter's distal end according to embodiments of the present invention.

Turning now to FIG. 2, the distal end 104 of the catheter's flexible shaft 102 is shown according to an embodiment of the present invention. An inner liner 202 forms an open lumen 204 of the catheter 100. The open lumen 204 is used as a conduit for catheter payloads. The inner liner 202 may be formed of a lubricious material to reduce friction of payloads.

An outer sheath 206 surrounds the inner liner 202. The outer sheath 206 provides a smooth outer surface for the flexible shaft 102. The outer sheath 206 may be formed of a lubricious material to reduce friction in some applications.

Between the outer sheath 206 and inner liner 202 are one or more steering lumens 208. The steering lumens 208 are specially shaped voids in the catheter wall that can accept a pressurized fluid. In this example, the steering lumens 208 are formed by a ribbed intermediate sheath 210 positioned between the inner liner 202 and outer sheath 206.

By pressurizing and depressurizing fluid within the steering lumens 208, the shape of the flexible shaft's distal end 104 can be altered enabling steering of the catheter 100. The steering lumens 208 are pressurized by one or more inflation lumens 212 that are in fluid connection with the steering lumens 208. The inflation lumens 212 can be pressurized and depressurized by injecting a saline solution (or other appropriate fluid) at a proximal access point of the catheter 100. By pressurizing an inflation lumen 212, the associated steering lumen 208 will expand. Likewise, depressurizing an inflation lumen 212 causes the associated steering lumen 208 to contract.

Figure 3:
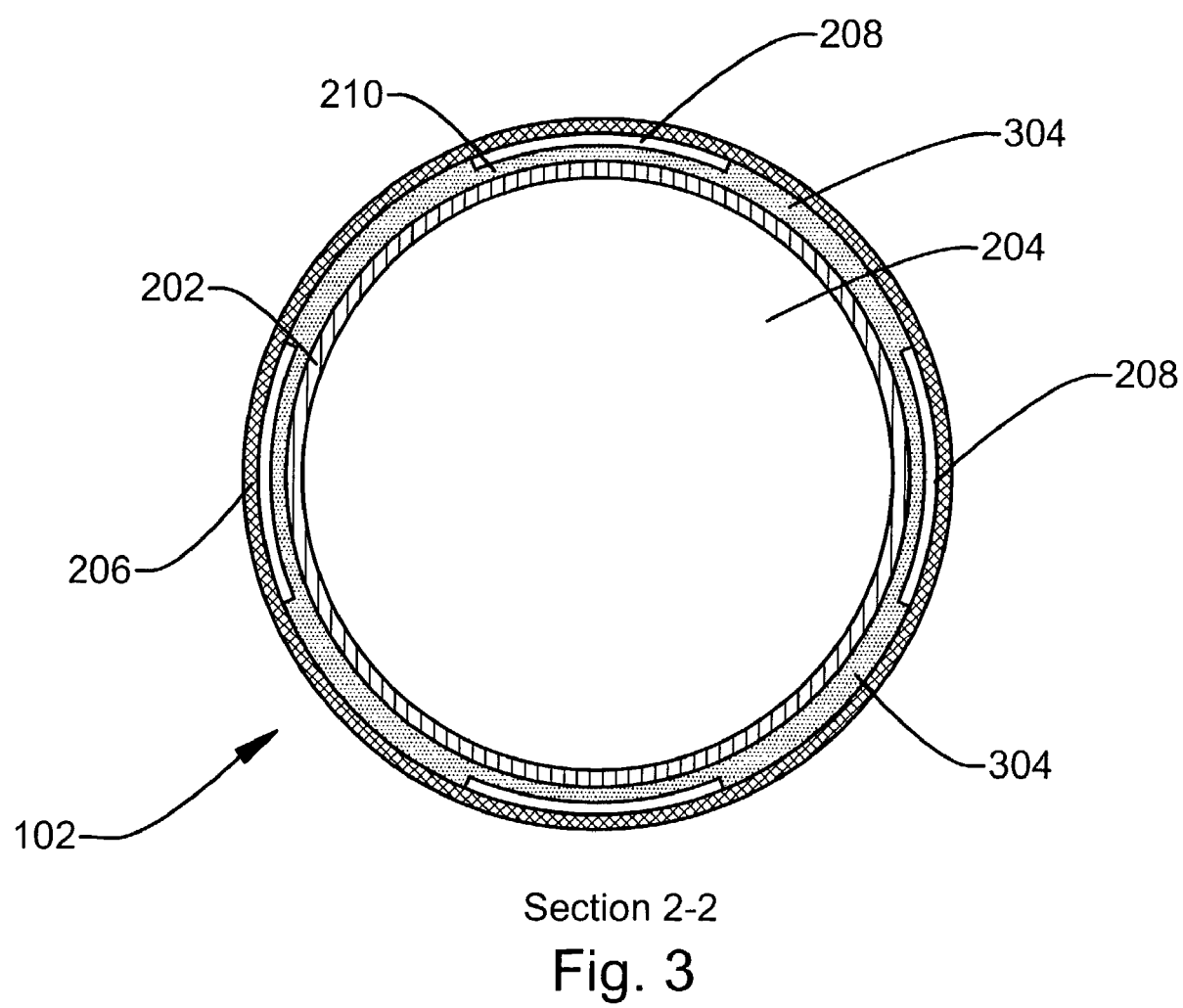
FIG. 3 is a cross sectional view of the guide catheter's distal end corresponding to section 2-2 of FIG. 2.

A cross sectional view of the flexible shaft 102 at the steering lumens 208 is shown in FIG. 3. In this example, four steering lumens 208 are formed by use of four ribs 304 on an intermediate sheath 210. It is appreciated that any number of steering lumens 208 may be formed by providing the appropriate number and size of ribs 304 on the intermediate sheath 210.

Although the steering lumens 208 in FIGS. 2 and 3 are shown formed by the layering of the inner, outer, and intermediate sheaths 202, 206, 210, it is appreciated that alternate sheath construction methods may be used to form the steering lumens 208. For example, a single extruded section may be used to form the steering lumen portion of the shaft 102, with proximal and distal portions bonded, molded, swaged, or otherwise attached to the steering lumen portion. The steering lumens 208 may be formed as voids between or within the inner and outer sheaths 202, 206. Whatever construction technique is implemented, the flexible shaft 102 will typically include an outer sheath 206 or similar covering to form a smooth outer surface.

The catheter shaft 102 may be constructed with a variable flexibility along its length. This allows the distal portions to be made flexible for maneuverability while the proximal portions are stiffer to enhance stability and torque transfer. This variation in flexibility can be obtained by varying cross sectional dimensions, varying material properties, adding stiffening elements such as a stainless steel braid, etc. A catheter shaft 102 according to the present invention may be also designed with particular flexibility characteristics near the steering lumen 208 to enhance steering effects. For example, the sections near the steering lumen 208 may allow for increased linear flexibility. This flexibility allows expansion and contractions of shaft walls when pressurizing and depressurizing the steering lumens 208. The steering lumen portion may have a variable flexibility, either lengthwise or at different circumferential portions, to tune the steering performance of the catheter shaft 102.

The catheter shaft 102 can be constructed using a variety of techniques known in the art. The shaft 102 can be formed of an extruded polymer, such as Pebax thermoplastic elastomer resin. Other polymer materials, such as nylon and polyurethane, are also commonly used for catheter guides. A proximal region of the shaft can be made stiffer than the distal region, providing kink resistance and enhanced transmission of axial forces and torque.

As shown in FIG. 2, the distal end 104 may include a pre-shaped curve. The pre-shaped curve may be located proximate the steering lumen 208 to enhance steering effects of the steering lumens 208. Various curve shapes are possible, the shapes being dictated by the destination vessel and access path of interest. The pre-shaped distal end 104 is made flexible such that the distal end 104 generally straightens while being guided through the vasculature, yet resumes the preformed shape when a wider cavity, such as a heart chamber, is reached.

The pre-shaped distal end 104 can be heat set to the desired shape during construction of the catheter shaft 102. In this fabrication method, the distal end 104 is held to the desired shape in a fixture while the assembly is thermally cycled to set the shape. Other methods can be used to pre-shape the distal end, such as embedding a shape member in the shaft. A wire made from a superelastic shape memory material such as Nitinol can be embedded in the shaft walls to impart a curve at the distal end 104.

Figure 4:
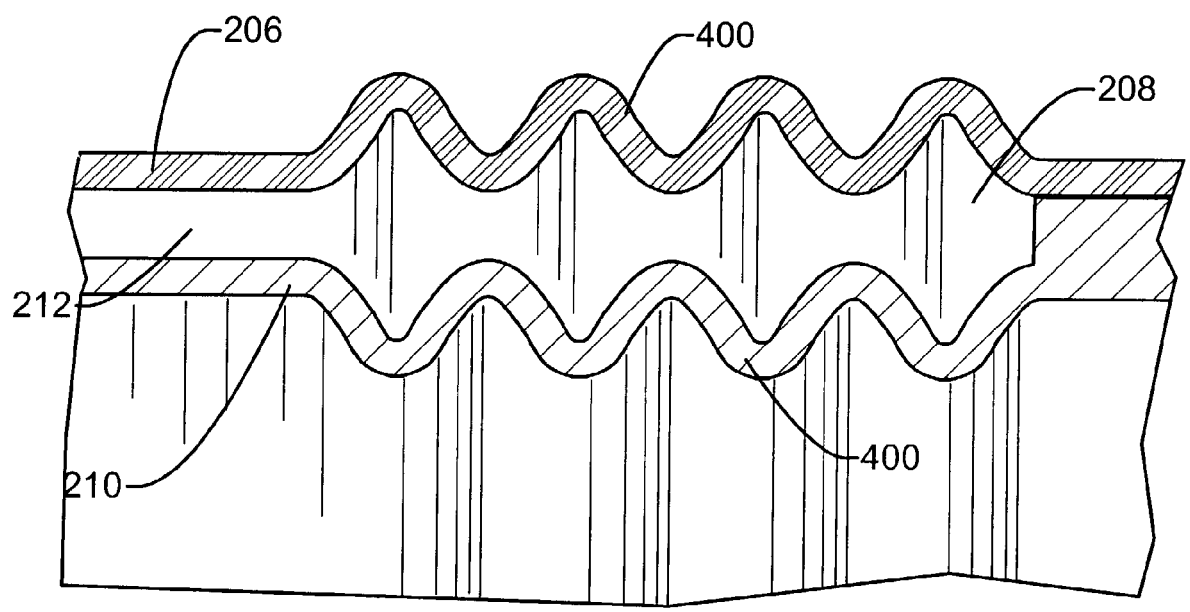
FIG. 4 is a cross sectional view of an alternate steering lumen according to an embodiment of the present invention.

Although the shaft walls shown in FIG. 2 are substantially smooth on both the inner and outer surfaces, other features may be added to assist in deflecting the distal end 104 in response to inflating the steering lumens 208. FIG. 4 shows an alternate embodiment of a steering lumen 208 formed in the flexible shaft 102.

In FIG. 4, a cross section of a shaft wall is shown. The steering lumen 208 is formed between corrugated portions 400 of the outer sheath 206 and the inner sheath 202. These corrugated portions 400 may be formed on the inner and/or outer surfaces of the shaft wall. The corrugated portions 400 may encompass the entire perimeter of the shaft wall (e.g. like a drinking straw), or the corrugated portions 400 may be formed on a portion of the shaft perimeter proximate the steering lumens 208. For example, an arrangement having four steering lumens 208 such as seen in the cross section of FIG. 3 may have corrugated portions 400 longitudinally arrayed only near the steering lumens 208, while the areas near the ribs 304 are smooth.

A clinician may utilize a guide catheter 100 according to the present invention for accessing various cavities within the body. The guide catheter 100 is used for cannulating cavities or blood vessels to serve as a conduit for placing drugs or devices in the body. In particular, the guide catheter 100 is well suited to access the coronary sinus. Coronary sinus access procedures are commonly required for implantation of pacing leads in the heart for treatment of congestive heart failure, for example. However, descriptions of coronary access using a catheter 100 according to the present invention are provided for purposes of illustration and not of limitation.

Referring again to FIG. 1, coronary sinus access typically involves introducing the distal tip of the catheter 100 through an incision 120 into an access vessel 122. Common access vessels include the right cephalic vein and the subclavian vein. The catheter 100 is advanced through access vessel 122 into the superior vena cava 106, thereby entering into the right atrium 101. From the right atrium 101, the catheter 100 can then locate the coronary sinus ostium 124, thereby readying the catheter 100 for introduction into the coronary sinus 108.

The clinician may use a fluoroscopic injection to help locate the coronary sinus ostium 124. Other sensors may also be used with or attached to the catheter 100 to assist in locating the ostium 124. For example, a Doppler/ultrasound sensor or thermal sensor may provide representations of the local heart structure to aid in guiding the catheter 100.

The catheter 100 can be maneuvered by extending and/or torquing a proximal end of the flexible shaft 102, thereby directing the guide's pre-formed distal end 104. By pressurizing and depressurizing steering lumens 110, the shape of the pre-formed distal end 104 can be altered to steer the catheter's distal tip until the coronary sinus ostium 124 is located.

After the ostium 124 is located, the flexible shaft 102 may be inserted into the ostium 124 to cannulate the coronary sinus 108. The steering lumens 110 may be inflated to assist in wedging the shaft into the coronary sinus 108. The catheter 100 may also include a separately inflatable occlusion balloon (not shown) on an outer surface of the shaft 102 for this purpose. Wedging the distal end of the shaft 102 into the coronary sinus 108 helps stabilized the shaft 102, as well as being useful for occluding blood flow for injection mapping branches of the coronary sinus (e.g., venography/angiography).

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guiding catheter for accessing a patient's heart, comprising:
   a flexible shaft having an open lumen and a pre-shaped distal portion;
   one or more inflatable steering lumens disposed within a wall of the flexible shaft proximate the pre-shaped distal portion; and
   one or more inflation lumen portions of the steering lumens in fluid connection with the steering lumens, the inflation lumen portions accessible at a proximal end of the shaft, wherein changing a fluid pressure of the steering lumens alters a shape of the pre-shaped distal end of the flexible shaft.

2. The guiding catheter of claim 1, wherein the wall of the flexible shaft comprise an inner liner and an outer sheath, the steering lumens disposed between the inner liner and the outer sheath.

3. The guiding catheter of claim 2, further comprising an intermediate sheath between the inner liner and the outer sheath, the intermediate sheath having one or more voids defining the steering lumens.

4. The guiding catheter of claim 3, wherein the intermediate sheath further comprises longitudinally disposed ribs defining the steering lumens.

5. The guiding catheter of claim 2, further comprising an intermediate sheath between the inner liner and the outer sheath, the intermediate sheath including a plurality of longitudinally disposed ribs defining the steering lumens.

6. The guiding catheter of claim 2, wherein the steering lumens comprise longitudinally disposed voids between the inner liner and the outer sheath.

7. The guiding catheter of claim 1, wherein the steering lumens are configured for independent inflation.

8. The guiding catheter of claim 1, wherein the one or more steering lumens comprise four steering lumens distributed around a perimeter of the flexible shaft.

9. A method of introducing a guide catheter into a destination vessel, comprising:
   introducing the guide catheter into an access vessel so that a distal end of the guide catheter is proximate the destination vessel;
   steering a distal tip of the guide catheter by changing a fluid pressure in one or more inflatable steering lumens within the guide catheter wall to change a shape of the distal end of the guide catheter; and
   cannulating the destination vessel with the distal end of the guide catheter.

10. The method of claim 9, wherein steering the distal tip of the guide catheter comprises independently changing the fluid pressure in one of the steering lumens.

11. The method of claim 9, further comprising inflating the steering lumens to seat the distal end of the guide catheter in the destination vessel after cannulating the destination vessel.

12. A guide catheter system, comprising:
   a flexible shaft having an open lumen and a pre-shaped distal end;
   means for inflatably steering the distal end of the flexible shaft disposed within a wall of the flexible shaft; and
   means, in fluid connection with the steering means, for pressurizing the steering means, wherein inflation of the steering means by the pressurization means causes a deformation of the pre-shaped distal end of the flexible shaft.

13. The guide catheter system of claim 12, wherein the steering means comprises a plurality of the steering means.

14. The guide catheter system of claim 13, wherein the plurality of the steering means are independently inflatable by the pressurization means.

15. A guiding catheter for accessing a patient's heart, comprising:
   a flexible shaft comprising:
      an inner lining having an open lumen;
      an outer sheath encompassing the inner lining;
      one or more inflatable steering lumens disposed between the inner lining and the outer sheath at a distal portion of the flexible shaft; and
      one or more inflation lumen portions of the steering lumens in fluid connection with the steering lumens, the inflation lumen portions accessible at a proximal end of the shaft, wherein changing a fluid pressure of the steering lumens causes a distal deflection of the flexible shaft.

16. The guiding catheter of claim 15, further comprising an intermediate sheath between the inner liner and the outer sheath, the intermediate sheath forming one or more voids defining the steering lumens.

17. The guiding catheter of claim 16, wherein the intermediate sheath further comprises longitudinally disposed ribs defining the steering lumens.

18. The guiding catheter of claim 15, wherein the steering lumens comprise longitudinally disposed voids between the inner liner and the outer sheath.

19. The guiding catheter of claim 15, wherein the steering lumens are independently inflatable.

20. The guiding catheter of claim 15, wherein the one or more steering lumens comprise four steering lumens equally distributed around a perimeter of the flexible shaft.

* * * * *